United States Patent
Chan et al.

(10) Patent No.: US 6,596,000 B2
(45) Date of Patent: *Jul. 22, 2003

(54) INSTRUMENT FOR POSITIONING AN INTRACORNEAL OPTICAL LENS

(75) Inventors: Kwan Y. Chan, Fort Worth, TX (US); David A. Eister, Mansfield, TX (US)

(73) Assignee: Alcon Universal Ltd., Hunenberg (CH)

( * ) Notice: Subject to any disclaimer, the term of this patent is extended or adjusted under 35 U.S.C. 154(b) by 22 days.

This patent is subject to a terminal disclaimer.

(21) Appl. No.: 09/954,091

(22) Filed: Sep. 17, 2001

(65) Prior Publication Data

US 2002/0042616 A1 Apr. 11, 2002

Related U.S. Application Data

(63) Continuation-in-part of application No. 09/467,411, filed on Dec. 20, 1999, now Pat. No. 6,290,705, and a continuation-in-part of application No. 09/467,462, filed on Dec. 20, 1999, and a continuation-in-part of application No. 09/434,912, filed on Nov. 5, 1999.

(51) Int. Cl.$^7$ .................................................. A61F 9/00
(52) U.S. Cl. ....................... 606/107; 606/205; 606/207; 606/210
(58) Field of Search ................................ 606/107, 205, 606/206, 210, 211, 160, 161, 166; 30/186, 191, 115, 116, 117, 304

(56) References Cited

U.S. PATENT DOCUMENTS

| | | | |
|---|---|---|---|
| 3,916,909 A | 11/1975 | Kletschka et al. | 128/354 |
| 3,980,086 A | * 9/1976 | Kletschka et al. | 604/35 |
| 4,225,667 A | 9/1980 | Ruben | 433/162 |
| 4,586,491 A | 5/1986 | Carpenter | 128/6 |
| 4,985,030 A | 1/1991 | Melzer et al. | 606/51 |
| 5,167,618 A | 12/1992 | Kershner | 604/22 |
| 5,195,541 A | 3/1993 | Obenchain | 128/898 |
| 5,209,747 A | 5/1993 | Knoepfler | 606/16 |
| 5,217,460 A | 6/1993 | Knoepfler | 606/52 |
| 5,217,464 A | * 6/1993 | McDonald | 606/107 |
| 5,222,960 A | 6/1993 | Poley | 606/107 |
| 5,271,379 A | 12/1993 | Phan et al. | 128/4 |
| 5,300,087 A | 4/1994 | Knoepfler | 606/207 |
| 5,630,821 A | * 5/1997 | Klaas | 606/107 |

(List continued on next page.)

FOREIGN PATENT DOCUMENTS

WO     WO 99/30645     6/1999

OTHER PUBLICATIONS

Grieshaber Forceps Brochures, Product Nos. 332, 500–555, 690–696, Feb. 1997, 5 pages.

Grieshaber "Instruments for Irrigation Aspiration" Brochure, Feb. 1997, 1 page.

Grieshaber Needle–holder Brochure, Product Nos. 750–755, Feb. 1997, 2 pages.

"Storz Instruments for Optometry" Catalog, Storz Ophthalmics, Oct. 1995, pp. 1, 4, 5.

*Primary Examiner*—Pedro Philogene
(74) *Attorney, Agent, or Firm*—W. David Lee

(57) ABSTRACT

An instrument for positioning an intracorneal optical lens within an intracorneal pocket is disclosed. The instrument generally includes a handle and a cannula associated with and having a distal portion extending from the handle. The cannula is for fluidly coupling to a vacuum source in a first mode of operation and to a reservoir of surgical fluid in a second mode of operation. The distal portion of the cannula is for receiving the lens in a folded position around the distal portion. The distal portion has an aperture for providing vacuum to hold the lens in the folded position in the first mode of operation and for ejecting surgical fluid in an outward direction from the distal portion to help unfold the lens in the second mode of operation. Methods of using the instrument for positioning of an intracorneal optical lens are also disclosed.

9 Claims, 5 Drawing Sheets

U.S. PATENT DOCUMENTS

| | | | |
|---|---|---|---|
| 5,665,100 A | 9/1997 | Yoon | 606/170 |
| 5,683,592 A | 11/1997 | Bartholomew et al. | 216/24 |
| 5,752,960 A * | 5/1998 | Nallakrishnan | 606/107 |
| 5,755,700 A | 5/1998 | Kritzinger et al. | 604/257 |
| 5,808,665 A | 9/1998 | Green | 348/65 |
| 5,860,985 A * | 1/1999 | Anschutz | 606/107 |
| 5,893,863 A | 4/1999 | Yoon | 606/170 |
| 5,897,507 A | 4/1999 | Kortenbach et al. | 600/562 |
| 5,919,202 A | 7/1999 | Yoon | 606/170 |
| 5,921,990 A | 7/1999 | Webb | 606/110 |
| 6,290,705 B1 * | 9/2001 | Chan et al. | 606/107 |

\* cited by examiner

INSTRUMENT FOR POSITIONING AN INTRACORNEAL OPTICAL LENS

This application is a continuation-in-part of U.S. application Ser. No. 09/467,411, filed Dec. 20, 1999 now U.S. Pat. No. 6,290,705, entitled "Irrigating Forceps"; U.S. application Ser. No. 09/467,462, filed Dec. 20, 1999, entitled "Lamellar Dissecting Instrument"; and U.S. application Ser. No. 09/434,912, filed Nov. 5, 1999, entitled "Lamellar Dissecting Instrument", all of which are incorporated herein in their entirety by this reference.

FIELD OF THE INVENTION

The present invention relates generally to microsurgical instruments and more specifically, but not by way of limitation, to microsurgical instruments suitable for the implantation of intracorneal optical lenses (ICOLs).

DESCRIPTION OF THE RELATED ART

The human eye in its simplest terms functions to provide vision by transmitting light through a clear outer portion called the cornea, and focusing the image by way of a crystalline lens onto a retina. The quality of the focused image depends on many factors including the size and shape of the eye, and the transparency of the cornea and the lens.

The optical power of the eye is determined by the optical power of the cornea and the crystalline lens. In the normal, healthy eye, sharp images are formed on the retina (emmetropia). In many eyes, images are either formed in front of the retina because the eye is abnormally long (axial myopia), or formed in back of the retina because the eye is abnormally short (axial hyperopia). The cornea also may be asymmetric or toric, resulting in an uncompensated cylindrical refractive error referred to as corneal astigmatism. In addition, due to age-related reduction in lens accommodation, the eye may become presbyopic resulting in the need for a bifocal or multifocal correction device.

In the past, axial myopia, axial hyperopia and corneal astigmatism generally have been corrected by spectacles or contact lenses, but there are several refractive surgical procedures that have been investigated and used since 1949. Barraquer investigated a procedure called keratomileusis that reshaped the cornea using a microkeratome and a cryolathe. This procedure was never widely accepted by surgeons. Another procedure that has been used is radial and/or transverse incisional keratotomy (RK or AK, respectively). Photoablative lasers have also been used to reshape the surface of the cornea (photorefractive keratectomy or PRK) or for mid-stromal photoablation (Laser-Assisted In Situ Keratomileusis or LASIK). All of these refractive surgical procedures cause an irreversible modification to the shape of the cornea in order to effect refractive changes, and if the correct refraction is not achieved by the first procedure, a second procedure or enhancement must be performed. Additionally, the long-term stability of the correction is variable because of the variability of the biological wound healing response between patients.

Permanent intracorneal implants made from synthetic materials are also known for the correction of corneal refractive errors. Such implants may be generally classified into two categories.

One category is intracorneal implants that have little or no refractive power themselves, but change the refractive power of the cornea by modifying the shape of the anterior surface of the cornea. U.S. Pat. No. 5,123,921 (Werblin, et al.); U.S. Pat. Nos. 5,505,722, 5,466,260, 5,405,384, 5,323,788, 5,318,047, 5,312,424, 5,300,118, 5,188,125, 4,766,895, 4,671,276 and 4,452,235 owned by Keravision and directed to intrastromal ring devices; and U.S. Pat. No. 5,090,955 (Simon), U.S. Pat. No. 5,372,580 (Simon, et al.), and WIPO Publication No. WO 96/06584 directed to Gel Injection Adjustable Keratoplasty (GLAK) all disclose examples of this category of implant.

A second category is intracorneal implants having their own refractive power. U.S. Pat. No. 4,607,617 (Choyce); U.S. Pat. No. 4,624,669 (Grendahl); U.S. Pat. No. 5,628,794 (Lindstrom); and U.S. Pat. Nos. 5,196,026 and 5,336,261 (Barrett, et al.) provide several examples of this category. In addition, U.S. patent application Ser. No. 08/908,230 filed Aug. 7, 1997 entitled "Intracorneal Diffractive Lens", which is incorporated herein in its entirety by reference, discloses an example of an ICOL that has both refractive and diffractive powers.

Microsurgical instruments used for the implantation of such intracorneal implants have also been developed. For example, WIPO Publication No. WO 99/30645 owned by Keravision discloses a variety of instruments for creating grooves in the stromal tissue for implanting a ring-shaped intracorneal implant or a pocket for implanting ICOLs. These tools may be used manually, but are preferably used in cooperation with a vacuum centering device. Another instrument used for creating an intracorneal pocket for implanting an ICOL is described in U.S. patent application Ser. No. 09/434,912 filed Nov. 5, 1999 entitled "Lamellar Dissecting Instrument", which is incorporated herein in its entirety by reference. However, after formation of an intracorneal pocket, an ICOL is typically positioned within the intracorneal pocket using conventional forceps, such as intraocular lens folding forceps. With conventional forceps, a surgeon must spend several minutes "spreading out" or flattening the ICOL within the intracorneal pocket and manipulating it into proper position within the pocket.

Accordingly, a need exists for a microsurgical instrument that more effectively positions an ICOL within an intracorneal pocket. The instrument should be easy for the surgeon to use, should maximize patient safety, and should be economically feasible.

SUMMARY OF THE INVENTION

One aspect of the present invention is an instrument for positioning an intracorneal optical lens within an intracorneal pocket. The instrument generally includes a handle and a cannula associated with and having a distal portion extending from the handle. The cannula is for fluidly coupling to a vacuum source in a first mode of operation and to a reservoir of surgical fluid in a second mode of operation. The distal portion of the cannula is for receiving the lens in a folded position around the distal portion. The distal portion has an aperture for providing vacuum to hold the lens in the folded position in the first mode of operation and for ejecting surgical fluid in an outward direction from the distal portion to help unfold the lens in the second mode of operation.

BRIEF DESCRIPTION OF THE DRAWINGS

For a more complete understanding of the present invention, and for further objects and advantages thereof, reference is made to the following description taken in conjunction with the accompanying drawings in which.

DETAILED DESCRIPTION OF THE PREFERRED EMBODIMENTS

The preferred embodiments of the present invention and their advantages are best understood by referring to FIGS. 1 through 7 of the drawings, like numerals being used for like and corresponding parts of the various drawings.

Figure 1:
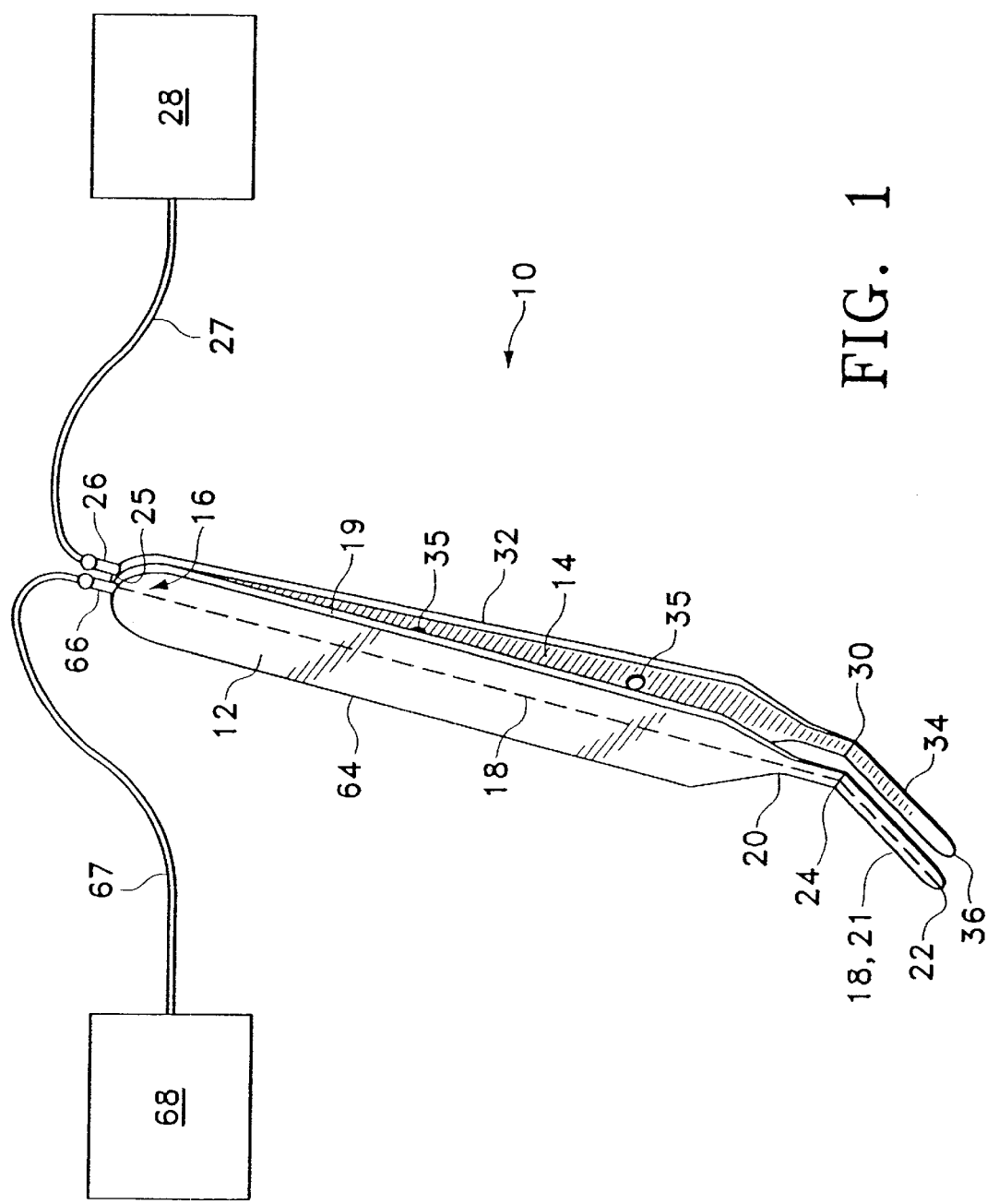
FIG. 1 is a perspective view schematically illustrating forceps according to a preferred embodiment of the present invention.

FIG. 1 illustrates microsurgical forceps 10 according to a preferred embodiment of the present invention. Forceps 10 are preferably used in the implantation of an intracorneal optical lens (ICOL) within an intracorneal pocket. However, forceps 10 may be used for positioning other lenses, devices, or implants within the eye or within other non-ocular body tissue. For convenience of description, but not by way of limitation, the present invention will be described hereinbelow with reference to implanting an ICOL within an intracorneal pocket.

Forceps 10 include an upper handle 12 and a lower handle 14 coupled at a hinge point 16. A cannula 18 is disposed within upper handle 12. Alternatively, although not shown in FIG. 1, cannula 18 may be coupled along a side of handle 12, such as side 19. Cannula 18 extends from the distal portion of upper handle 12 at a point 20. This portion of cannula 18 forms an upper jaw 21 of forceps 10. Cannula 18 preferably has a rounded end 22 and a bend 24. The portion of cannula 18 disposed within upper handle 12 and the portion of cannula 18 extending beyond bend 24 are preferably disposed at an angle of about 120 degrees to about 150 degrees relative to one another to facilitate the use of forceps 10 by a surgeon. Cannula 18 also extends from a proximal end 25 of forceps 10 and terminates in a port 26. Port 26 is for fluidly coupling with a reservoir 28. Such coupling is preferably performed using medical grade silastic tubing 27. Reservoir 28 may comprise a syringe, a pumping device, or other conventional apparatus for providing pressurized surgical fluid. Surgical fluid 18 may be saline solution, BSS PLUS® intraocular irrigating solution available from Alcon Laboratories, Inc. of Fort Worth, Tex., or another irrigating solution.

Lower handle 14 is formed with a bend 30 so as to mate with a bottom surface of upper handle 12. Lower handle 14 has a proximal portion 32 above bend 30 and a lower jaw 34 extending beyond bend 30. Lower jaw 34 preferably has a rounded end 36. Proximal portion 32 and lower jaw 34 are preferably disposed at an angle of about 120 degrees to about 150 degrees relative to one another.

When a user squeezes upper handle 12 and lower handle 14 together, upper jaw 21 and lower jaw 34 move toward one another. When a user quits exerting such pressure on upper handle 12 and lower handle 14, upper jaw 21 and lower jaw 34 move away from one another to a natural, unbiased spacing determined by the geometry and material properties of forceps 10. When a user squeezes upper handle 12 and lower handle 14 completely together, upper jaw 21 and lower jaw 34 are preferably spaced about 0.1 mm apart. This spacing corresponds to the typical thickness of an ICOL. Stops 35 may be disposed on the internal surface of proximal portion 32 of lower handle 14 or the internal surface of upper handle 12 to facilitate this spacing.

Upper jaw 21 preferably has a length of about 12 mm beyond bend 24, a width of about 1.0 mm, and a thickness of about 0.6 mm. Lower jaw 34 preferably has a length of about 15 mm beyond bend 30, a width of about 1.0 mm, and a thickness of about 0.6 mm. Upper handle 12 and lower handle 14 preferably have a length of about 8.4 cm and a width of about 1 cm. Forceps 10, including cannula 18, are preferably formed from stainless steel.

Figure 2:
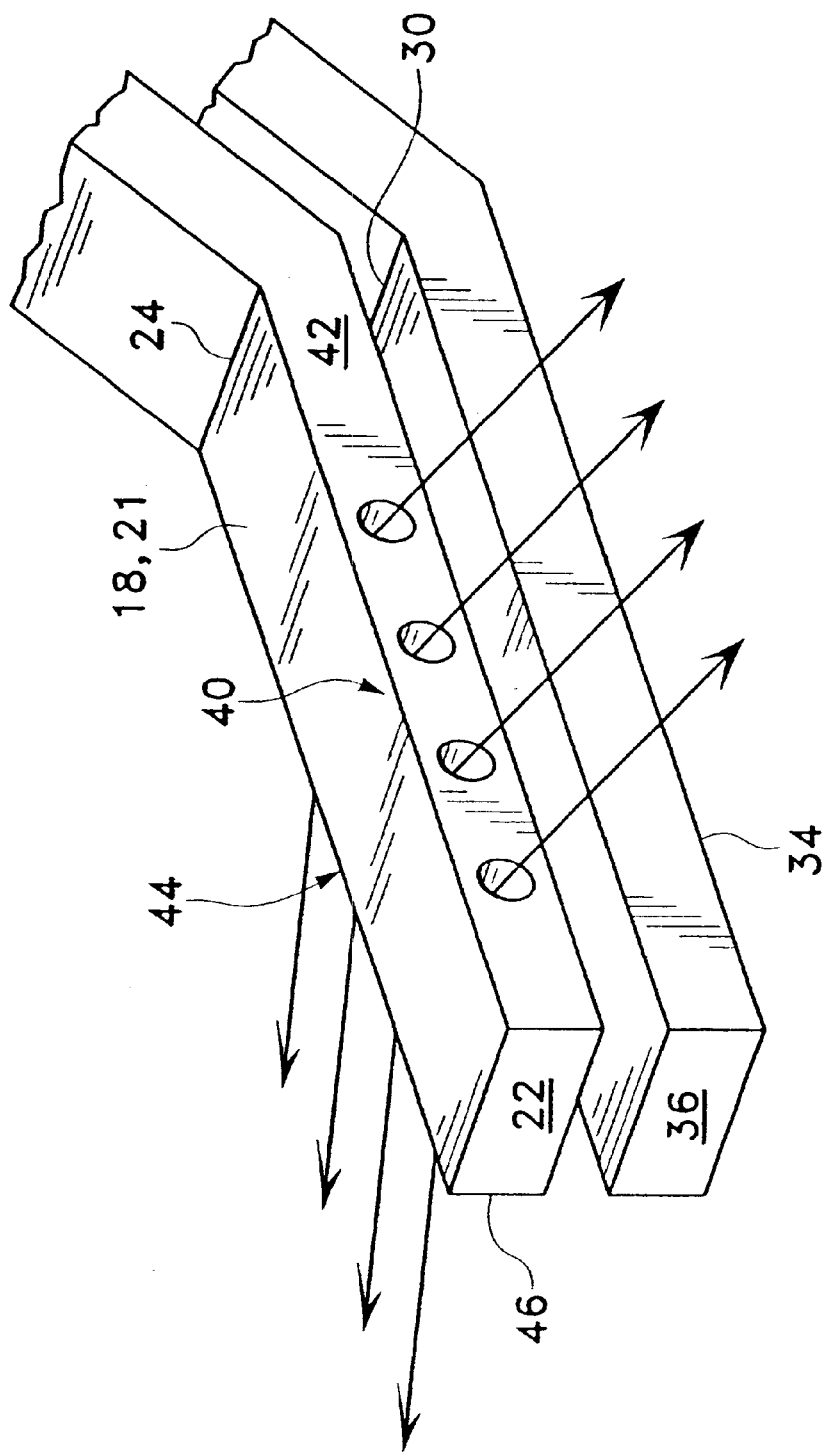
FIG. 2 is an enlarged, fragmentary view of the upper and lower jaws of the forceps of FIG. 1.
Figure 4:
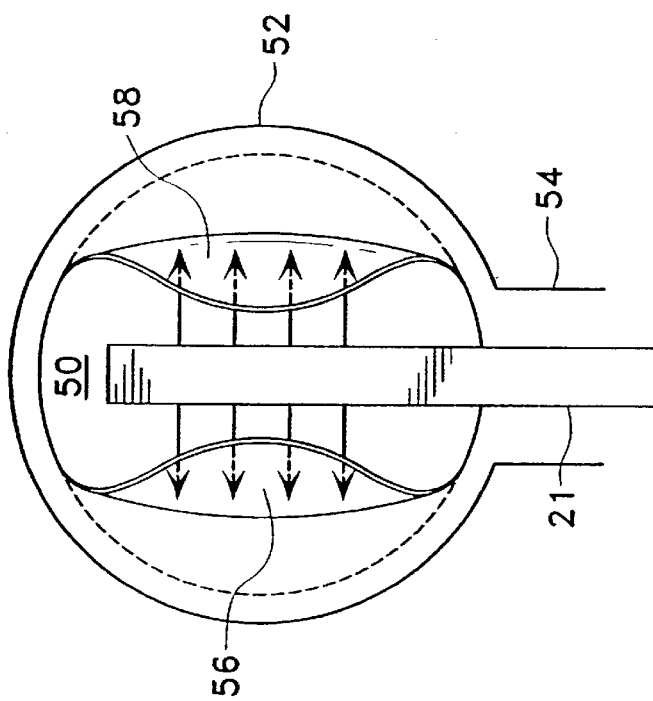
FIG. 4 is an enlarged, top, fragmentary view schematically illustrating the positioning of an ICOL within an intracorneal pocket using the forceps of FIG. 1.

FIG. 2. illustrates an enlarged view of a preferred embodiment of upper jaw 21 (and thus the distal end of cannula 18) and lower jaw 34. As shown in FIG. 2, upper jaw 21 preferably has a generally rectangular cross-section. Upper jaw 21 has a plurality of spaced apertures 40 on a side 42 and a plurality of spaced apertures 44 (not visible in FIG. 2) on a side 46. Upper jaw 21 preferably has four apertures 40 having a diameter of about 0.2 mm and a spacing of about 1 mm to about 2 mm between each aperture. Apertures 44 preferably have an identical geometry and spacing to apertures 40.

Referring now to FIGS. 1–4, the preferred method of using forceps 10 to position an ICOL within an intracorneal pocket will now be described in greater detail. A human eye has a cornea having a diameter of about 12 mm. Therefore, the diameter of an ICOL 50 must be less than 12 mm, is preferably from about 5 mm to about 9 mm, and is most preferably about 7 mm. Intracorneal pocket 52 for receiving ICOL 50 preferably has a diameter about 1 mm larger than the diameter of ICOL 50. For the preferred diameter of ICOL 50 of 7 mm, intracorneal pocket 52 has a diameter of about 8 mm. Intracorneal pocket 52 is accessed via a conventional tunnel incision 54. Tunnel incision 54 preferably has a width of about 3 mm, a length of about 1.5 mm, and a depth of about 0.25 mm to about 0.3 mm from the outer surface of the cornea. A preferred method of forming intracorneal pocket 52, including tunnel incision 54, is described in more detail in U.S. application Ser. No. 09/434,912 mentioned hereinabove. For convenience of description, but not by way of limitation, the preferred method of using forceps 10 to position an ICOL within an intracorneal pocket will be described with reference to an intracorneal pocket 52 having a diameter of about 8 mm, a tunnel incision 54 having a width of about 3 mm, and an ICOL having a diameter of about 7 mm.

During the procedure, a surgeon first places ICOL 50 on a sterile surface in its proper orientation for insertion into the eye. The surgeon grasps ICOL 50 proximate its midline with upper jaw 21 and lower jaw 34 of forceps 10, insuring that the rounded, distal end 22 of upper jaw 21 and the rounded, distal end 36 of lower jaw 34 are proximate the far edge of ICOL 50.

The following steps are performed using an operating microscope to visualize the anterior aspect of the eye and after applying a topical anesthetic to the eye. Jaws 21 and 34, and ICOL 50, are positioned proximate the entrance of tunnel incision 54. The surgeon utilizes conventional forceps (not shown) to "prime" edges 56 and 58 of ICOL 50 to fold upwards while using forceps 10 to insert ICOL 50 into tunnel incision 54 in the direction of arrow 60. After passing through tunnel incision 54, ICOL 50 is then centered within intracorneal pocket 52.

The surgeon then activates reservoir 28 to provide surgical fluid to upper jaw 21 via cannula 18. Surgical fluid is ejected from apertures 40 and 44 of upper jaw 21 with enough force to spread, or to help spread, folded edges 56 and 58 of ICOL 50 into their proper flattened orientation, as indicated by dashed lines in FIG. 4. Apertures 40 and 44 are preferably formed so that a stream of fluid is ejected from each aperture for a distance of about 1 cm. The streams of surgical fluid ejected from apertures 40 and 44 are indicated by bolded arrows in FIGS. 2 and 4. Apertures 40 and 44 are preferably oriented so that the streams of surgical fluid are ejected at a downward angle of about 30 to about 45 degrees relative to the plane of upper jaw 21. The surgical fluid lubricates ICOL 50 and intracorneal pocket 52 during the unfolding of ICOL 50, minimizing any irritation of the stromal tissues. The surgical fluid also lubricates forceps 10, minimizing any irritation of the stromal tissues upon withdrawal of forceps 10.

After ejecting surgical fluid, the surgeon then makes a final positioning of ICOL 50 and withdraws forceps 10 from tunnel incision 54. Any excess surgical fluid drains out of intracorneal pocket 52 from tunnel incision 54 into the exterior of the cornea. A topical antibiotic/steroid is preferably placed in the eye after implantation of ICOL 50.

Using forceps 10, it has been observed that a surgeon may properly position ICOL 50 within intracorneal pocket 52 as described hereinabove in less than 30 seconds. In contrast, such positioning typically requires about 1.5 to 3 minutes using conventional intraocular lens folding forceps.

Figure 5:
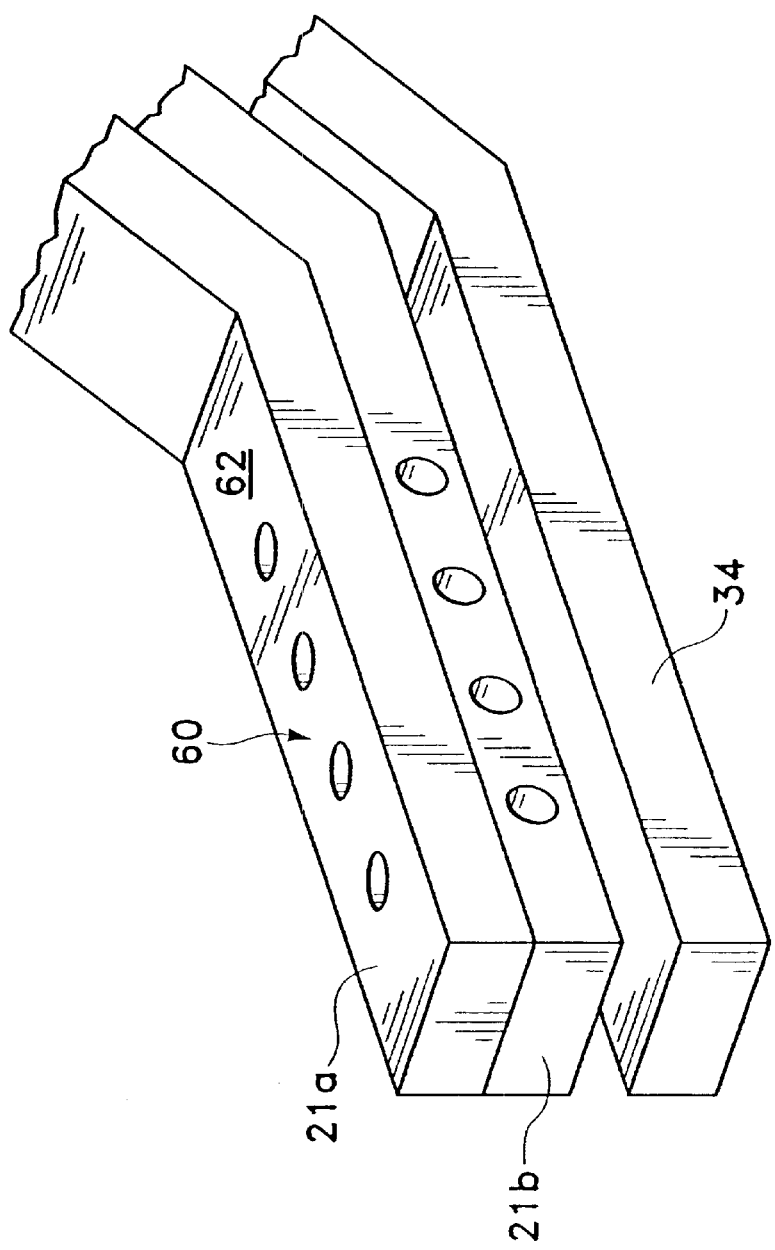
FIG. 5 is an enlarged, fragmentary view of a second preferred embodiment of the upper and lower jaws of the forceps of FIG. 1.

Referring now to FIG. 5, an enlarged view of a second preferred embodiment of the upper and lower jaws of forceps 10 is schematically illustrated. In this embodiment, forceps 10 has a first upper jaw portion 21*a*, a second upper jaw portion 21*b* disposed below upperjaw portion 21*a*, and a lower jaw 34. Upper jaw portion 21*b* preferably has an identical structure and operation as upper jaw 21 of FIGS. 1–4. Lower jaw 34 preferably has an identical structure and operation as lower jaw 34 of FIGS. 1–4. Upper jaw portion 21*a* has a structure similar to upper jaw 21 of FIGS. 1–4, except that upper jaw portion 21*a* has plurality of spaced apertures 60 on an upper surface 62 instead of a plurality of apertures 40 and 44 on its sides 42 and 46. Upper jaw portion 21*a* preferably has four apertures 60 having a diameter of about 0.2 mm and a spacing of about 1 mm to about 2 mm between each aperture.

Referring to FIG. 1, upper jaw portion 21*a* is preferably a distal end of a second cannula (not shown) similar to cannula 18. This second cannula may be disposed within, or coupled to a side 64, of upper handle 12. The proximal end of this second cannula extends from proximal end 25 of forceps 10 and terminates in a port 66. Port 66 is for fluidly coupling with a vacuum source 68. Such coupling is preferably performed using medical grade silastic tubing 67. Vacuum source 68 may comprise a syringe, a venturi coupled to a pneumatic pressure source, a pumping device, or another conventional source of vacuum.

Figure 3:
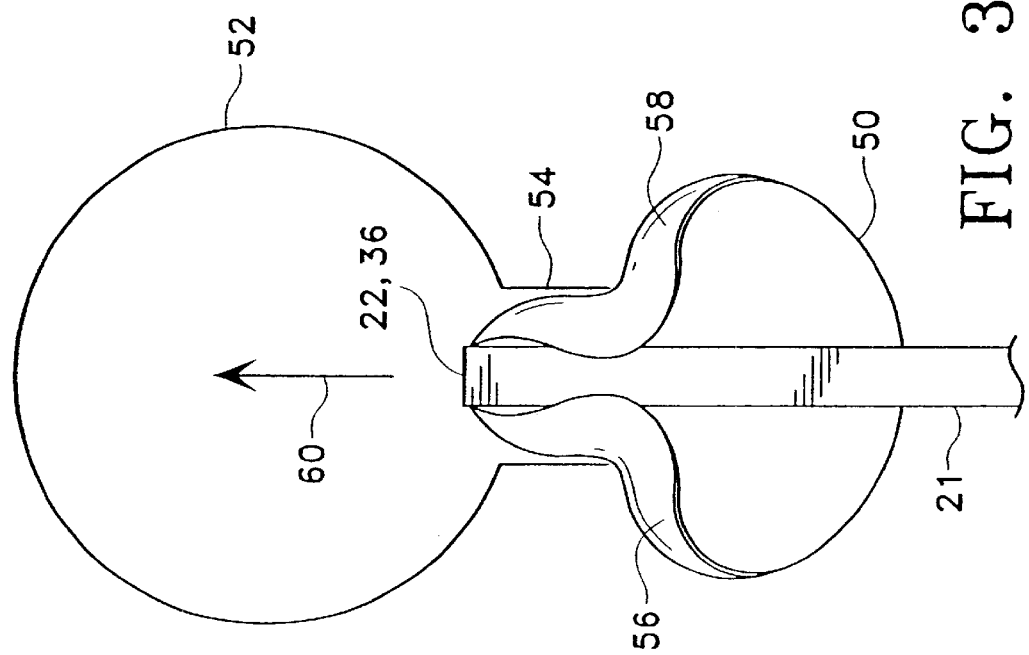
FIG. 3 is an enlarged, top, fragmentary view schematically illustrating the insertion of an ICOL into an intracorneal pocket using the forceps of FIG. 1.

Referring to FIGS. 1, 3, and 5, when "priming" edges 56 and 58 of ICOL 50 to fold upwards, the surgeon may activate vacuum source 68. Vacuum is supplied to apertures 60 of upperjaw 21*a*, insuring that edges 56 and 58 remain in a folded position. Upper jaw 21*a* thus facilitates the insertion of ICOL 50 through tunnel incision 54 and minimizes any irritation of stromal tissue. Once ICOL 50 is centered within intracorneal pocket 52, the surgeon deactivates vacuum source 68. The surgeon then activates reservoir 28 to eject surgical fluid to flatten ICOL 50, as described above. If the explanting of ICOL 50 is necessary at a later time, upper jaw 21*a* may also be used to insure that edges 56 and 58 remain in a folded position as ICOL passes through tunnel incision 54.

Figure 6:
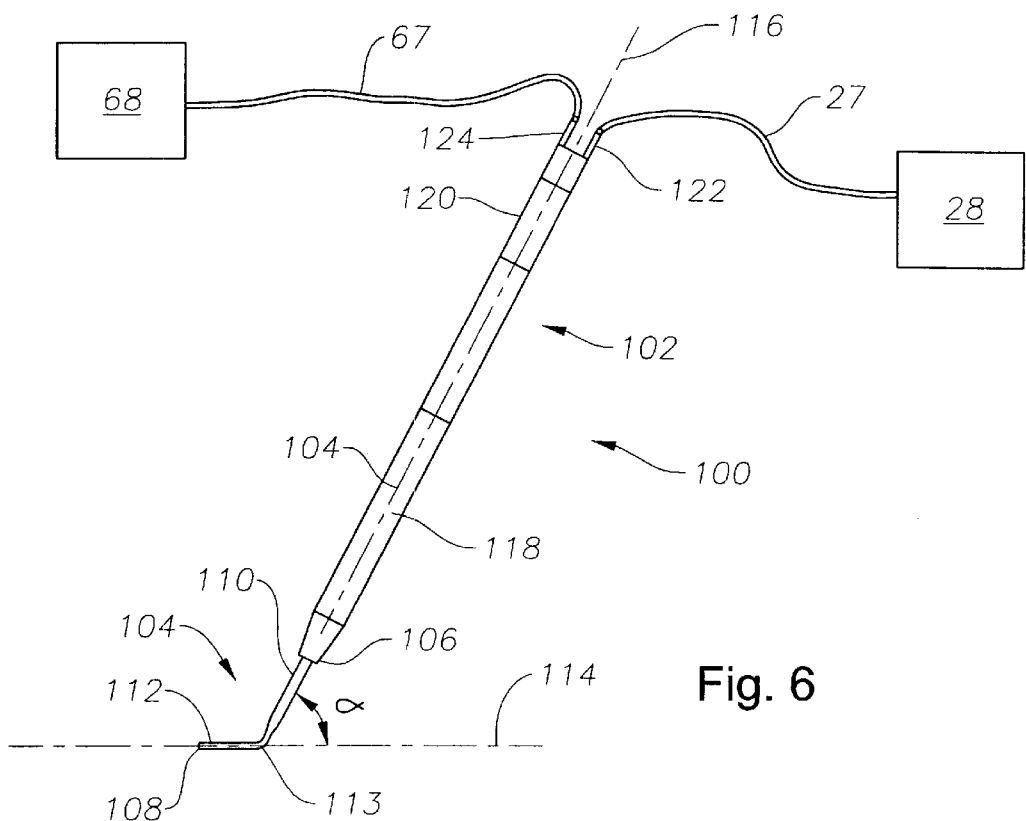
FIG. 6 is a perspective view schematically illustrating another instrument for implantation of an intracorneal optical lens according to a preferred embodiment of the present invention.
Figure 7:
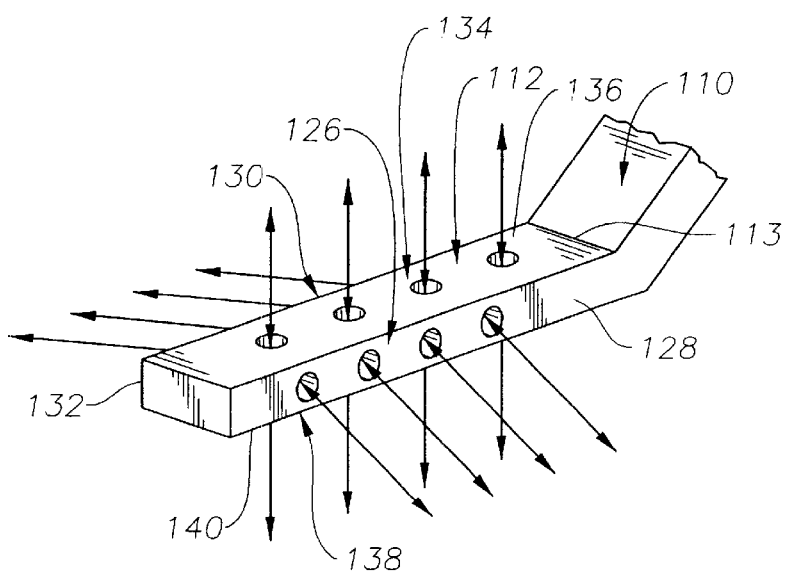
FIG. 7 is an enlarged, fragmentary view of the distal portion of the instrument of FIG. 6 according to a preferred embodiment of the present invention.

FIGS. 6–7 illustrate a preferred embodiment of an instrument 100 for implantation of intracorneal optical lens within an intracorneal pocket. Instrument 100 generally includes a handle 102 and a cannula 104. Cannula 104 is preferably disposed within handle 102. Alternatively, although not shown in FIG. 6, cannula 104 may be coupled along the exterior of handle 102. Cannula 104 extends from the distal end of handle 102 at a point 106.

The portion of cannula 104 extending from handle 102 generally includes a proximal portion 110 and a distal portion 112 separated by a bend 113. Distal portion 112 preferably has a rounded end 108 and a longitudinal axis 114. Proximal portion 110, handle 102, and the portion of cannula 104 within handle 102 preferably have a common longitudinal axis 116. Distal portion 112 is preferably oriented at an angle α with respect to proximal portion 110 and handle 102. Angle α is preferably from about 30 degrees to about 60 degrees, and is most preferably about 45 degrees. Distal portion 112 preferably has a length of about 12 mm, a width of about 1.0 mm to about 2.5 mm, and a thickness of about 0.6 mm. Cannula 104 is preferably formed from surgical stainless steel.

Handle 102 preferably has a generally cylindrical geometry and preferably includes a region 118 having a knurled or roughened surface to facilitate the gripping of instrument 100. Handle 102 may also have a generally flat region 120 that allows instrument 100 to be marked with identifying data. Handle 102 is preferably made out of conventional thermoset polymeric materials. Handle 102 may alternatively be formed from surgical stainless steel or other conventional materials used to form microSurgical instruments, if desired. Handle 102 also includes two ports 122 and 124. Port 122 is for fluidly coupling with reservoir 28 via tubing 27. Port 124 is for fluidly coupling with vacuum source 68 via tubing 67. Both ports 122 and 124 are fluidly coupled with cannula 104.

FIG. 7 illustrates an enlarged view of a preferred embodiment of distal portion 112 of cannula 104. As shown in FIG. 7, distal portion 112 preferably has a generally rectangular cross-section. Alternatively, distal portion 112 may have a generally circular or other polygonal cross-section, if desired. Distal portion 112 preferably has a plurality of spaced apertures 126 on a side 128 and a plurality of spaced apertures 130 (not visible in FIG. 7) on a side 132. Distal portion 112 preferably has four apertures 126 having a diameter of about 0.2 mm and a spacing of about 1 mm to about 2 mm between each aperture. Apertures 130 preferably have an identical geometry and spacing to apertures 126. Distal portion 112 preferably also has a plurality of spaced apertures 134 on an upper surface 136. Distal portion 112 may also have a plurality of spaced apertures 138 (not visible in FIG. 7) on a lower surface 140. Distal portion 112 preferably has four apertures 134 having a diameter of about 0.2 mm and a spacing of about 1 mm to about 2 mm between each aperture. Apertures 138 preferably have an identical geometry and spacing to apertures 134.

Referring to FIGS. 3–4 and 6–7, the preferred method of using instrument 100 to position ICOL 50 within intracorneal pocket 52 will now be described in greater detail. The reader will understand that when viewing FIGS. 3–4, instrument 100 is used instead of forceps 10.

During the procedure, a surgeon first places ICOL 50 on a sterile surface in its proper orientation for insertion into the eye. The surgeon then lays distal portion 112 over the upper surface of ICOL 50, insuring that the rounded, distal end 108 of distal portion 112 is proximate the far edge of ICOL 50. The surgeon then uses conventional forceps to fold ICOL 50 around distal portion 112 so that edges 56 and 58 rest upon upper surface 136. The surgeon then activates vacuum source 68 to supply vacuum to apertures 126, 130, 134, and 138 of distal portion 112 via cannula 104. This vacuum holds ICOL 50 in a folded position around distal portion 112.

The following steps are then performed using an operating microscope to visualize the anterior aspect of the eye and after applying a topical anesthetic to the eye. Distal portion 112, and ICOL 50, are positioned proximate the entrance of tunnel incision 54. The surgeon uses instrument 100 to insert ICOL 50 into tunnel incision 54 in the direction of arrow 60. After passing through tunnel incision 54, ICOL 50 is then centered within intracorneal pocket 52. The surgeon then deactivates vacuum source 68.

The surgeon then activates reservoir 28 to provide surgical fluid to distal portion 112 via cannula 104. Surgical fluid is ejected from apertures 126, 130, 134, and 138 of distal portion 112 with enough force to spread, or to help spread, folded edges 56 and 58 of ICOL 50 into their proper flattened orientation, as indicated by dashed lines in FIG. 4. Apertures 126, 130, 134, and 138 are preferably formed so that a stream of fluid is ejected from each aperture for a distance of about 1 cm. The streams of surgical fluid ejected from apertures 126 and 130 are indicated by bolded arrows in FIGS. 4 and 7. Apertures 126 and 130 are preferably oriented so that the streams of surgical fluid are ejected at a downward angle of about 30 to about 45 degrees relative to the plane distal portion 112, as shown in FIG. 7. Apertures 134 and 138 are preferably oriented so that the streams of surgical fluid are ejected generally perpendicular to the plane of upper surface 136 and lower surface 140. The surgical fluid lubricates ICOL 50 and intracorneal pocket 52 during the unfolding of ICOL 50, minimizing any irritation of the stromal tissues. The surgical fluid also lubricates instrument 100, minimizing any irritation of the stromal tissues upon withdrawal of forceps 100.

After ejecting surgical fluid, the surgeon then makes a final positioning of ICOL 50 with rounded end 108 of distal portion 112 and withdraws instrument 100 from tunnel incision 54. Any excess surgical fluid drains out of intracorneal pocket 52 from tunnel incision 54 into the exterior of the cornea. A topical antibiotic/steroid is preferably placed in the eye after implantation of ICOL 50. Using instrument 100, it is believed that a surgeon may properly position ICOL 50 within intracorneal pocket 52 with minimal trauma to the stromal bed due to the small cross-section of distal portion 112.

In addition, it is believed that a surgeon may use instrument 100 to facilitate the explanting of an ICOL if such explanting is necessary at a later time. In this case, a surgeon reopens the entrance to tunnel incision 54 with a conventional knife, inserts distal portion 112 of cannula 104 into tunnel incision 54, and activates reservoir 28 to eject surgical fluid from apertures 126, 130, 134, and 138. The ejected surgical fluid helps to separate tissues along the original tunnel incision 54 and reopen the tunnel incision. The surgeon may also insert distal portion 112 into intracorneal pocket 52 above, below, or both above and below ICOL 50 and activate reservoir 28 to eject surgical fluid from apertures 126, 130, 134, and 138 in each case. The ejected surgical fluid helps to separate tissues within original intracorneal pocket 52 and reopen the pocket. The surgeon may also use rounded end 108 of distal portion 112 to separate tissues within tunnel incision 54 or intracorneal pocket 52. After reopening of intracorneal pocket 52 and/or tunnel incision 54, the surgeon preferably removes ICOL 50 from intracorneal pocket 52 and tunnel incision 54 using conventional forceps.

From the above, it may be appreciated that the present invention provides a microsurgical instrument that more effectively positions an ICOL within an intracorneal pocket. The instrument is easy for a surgeon to use, safe for the patient, and is relatively inexpensive.

The present invention is illustrated herein by example, and various modifications may be made by a person of ordinary skill in the art. For example, the geometries of the upper handle, lower handle, upper jaw, and lower jaw of the forceps may be different from that shown in the preferred embodiments. As another example, the length of the upper and lower jaws of the forceps, or the distal portion 112 of cannula 104 of instrument 100, may be changed to accommodate ICOLs and intracorneal pockets having various diameters. As a further example, apertures 60 may be located on the sides of upper jaw portion 21a. As a further example, apertures 60 may be located on lower jaw 34, and the cannula associated with apertures 60 may be disposed on or within proximal portion 32 of lower handle 14. As a further example, the forceps may be formed with only vacuum capability instead of only irrigating capability, or irrigating and vacuum capabilities, for certain applications of the present invention. As a further example, cannula 18 or cannula 104 may be used to deliver a liquid pharmaceutical preparation. As a further example, the positions of upper jaw 21 and lower jaw 34, or upper jaw portions 21a and 21b and lower jaw 34, as shown in FIGS. 2 and 5 may be reversed in cases where the ICOL is "primed" by folding its sides downward instead of upward. In this case, apertures 42 and 44 are preferably oriented so that streams of surgical fluid are ejected at an upward angle relative to the plane of the jaws of the forceps. In addition, upper jaw portion 21b is preferably located above upper jaw portion 21a, and apertures 60 of upper jaw portion 21a are preferably located on its lower surface. As a final example, ICOL 50 may be folded around distal portion 112 of cannula 104 of instrument 100 so that edges 56 and 58 rest upon lower surface 140 of distal portion 112. In this case, apertures 126 and 130 are preferably oriented so that the streams of surgical fluid are ejected at an upward angle of about 30 to about 45 degrees relative to the plane distal portion 112.

It is believed that the operation and construction of the present invention will be apparent from the foregoing description. While the apparatus and methods shown or described above have been characterized as being preferred, various changes and modifications may be made therein without departing from the spirit and scope of the invention as defined in the following claims.

What is claimed is:

1. An instrument for positioning an intracorneal optical lens within an intracorneal pocket, comprising:
    a handle; and
    a cannula associated with and having a distal portion extending from said handle, said cannula for fluidly coupling to a vacuum source in a first mode of operation and to a reservoir of surgical fluid in a second mode of operation, said distal portion for receiving said lens in a folded position around said distal portion, and said distal portion having an aperture for providing vacuum to hold said lens in said folded position in said first mode of operation and for ejecting said surgical fluid in an outward direction from said distal portion to help unfold said lens in said second mode of operation.

2. The instrument of claim 1 further comprising a plurality of said apertures and wherein:

said distal portion comprises a first side, a second side, and an upper surface, and at least one of said plurality of said apertures is on each of said first side, said second side, and said upper surface.

3. The instrument of claim 2 wherein:

said distal portion comprises a lower surface; and at least one of said plurality of apertures is on said lower surface.

4. The instrument of claim 2 wherein at least two of said plurality of said apertures are on each of said first side, said second side, and said upper surface.

5. The instrument of claim 3 wherein at least two of said plurality of said apertures are on each of said first side, said second side, said upper surface, and said lower surface.

6. A method of positioning an intracorneal optical lens within an intracorneal pocket, comprising the steps of:

providing a microsurgical instrument, comprising:

a handle; and a cannula associated with and having a distal portion extending from said handle, said cannula for fluidly coupling to a vacuum source in a first mode of operation and to a reservoir of surgical fluid in a second mode of operation, said distal portion having an aperture for providing vacuum in said first mode of operation and for ejecting said surgical fluid in said second mode of operation;

folding said lens around said distal portion;

activating said vacuum source so that said aperture provides vacuum to hold said lens in a folded position;

inserting said lens into said intracorneal pocket in said folded position;

deactivating said vacuum source; and activating said reservoir so that said aperture ejects said surgical fluid to help unfold said lens into a generally flattened position within said intracorneal pocket.

7. The method of claim 6 wherein:

said distal portion comprises a first aperture oriented in a first direction, and a second aperture oriented in a second direction opposite said first direction;

said step of activating said vacuum source comprises providing said vacuum through said first aperture and said second aperture; and said step of activating said reservoir comprises ejecting said surgical fluid from said first aperture and said second aperture.

8. The method of claim 7 wherein:

said distal portion comprises a third aperture oriented in a third direction, said third direction being generally perpendicular to said first direction and said second direction;

said step of activating said vacuum source comprises providing said vacuum through said third aperture; and said step of activating said reservoir comprises ejecting said surgical fluid from said third aperture.

9. The method of claim 8 wherein:

said distal portion comprises a fourth aperture oriented in a fourth direction opposite said third direction;

said step of activating said vacuum source comprises providing said vacuum through said fourth aperture; and said step of activating said reservoir comprises ejecting said surgical fluid from said fourth aperture.

* * * * *

UNITED STATES PATENT AND TRADEMARK OFFICE
CERTIFICATE OF CORRECTION

PATENT NO. : 6,596,000 B2  Page 1 of 1
DATED : July 22, 2003
INVENTOR(S) : Chan, Kwan Y. and Eister, David A.

It is certified that error appears in the above-identified patent and that said Letters Patent is hereby corrected as shown below:

Column 1,
Line 63, delete "intracomeal" and insert -- intracorneal -- in its place.

Column 2,
Lines 8, 19, 23 and 26, delete "intracomeal" and insert -- intracorneal -- in its place.
Line 14, delete "Intracomeal" and insert -- Intracorneal -- in its place.

Column 8,
Lines 62 and 63, delete "intracomeal" and insert -- intracorneal -- in its place.

Column 9,
Line 27, delete "intracomeal" and insert -- intracorneal -- in its place.

Signed and Sealed this

Ninth Day of December, 2003

JAMES E. ROGAN
*Director of the United States Patent and Trademark Office*